United States Patent [19]

Bognar et al.

[11] 4,167,636
[45] Sep. 11, 1979

[54] 7,8-DIHYDROISOMORPHINE DERIVATIVE, NAMELY AZIDOETHYLMORPHINE

[75] Inventors: Rezso Bognar; Sandor Makleit; Geza Kiss; Sandor Berenyi; Terez Mile, all of Debrechen; Jozsef Knoll, Budapest; Sandor Elek, Tiszavasvari; Istvan Gyoker, Tiszavasvari; Attila Zoltai, Tiszavasvari; Gyorgy Toth, Tiszavasvari; Laszlo Litkei, Tiszavasvari, all of Hungary

[73] Assignee: Chinoin Gyogyszer es Vegyeszeti, Budapest, Hungary

[21] Appl. No.: 891,195

[22] Filed: Mar. 29, 1978

Related U.S. Application Data

[63] Continuation of Ser. No. 681,214, Apr. 28, 1976, abandoned, which is a continuation-in-part of Ser. No. 502,729, Sep. 3, 1974, abandoned.

[30] Foreign Application Priority Data

Sep. 4, 1973 [HU] Hungary .................................... 13616

[51] Int. Cl.$^2$ ................. C07D 489/00; A61K 31/485
[52] U.S. Cl. ....................................... 546/46; 424/260
[58] Field of Search ........................... 260/285; 546/46

[56] References Cited

U.S. PATENT DOCUMENTS

| | | | |
|---|---|---|---|
| 3,880,862 | 4/1975 | Meltzer | 260/285 |
| 3,880,863 | 4/1975 | Meltzer | 260/285 |
| 3,882,127 | 5/1975 | Meltzer | 260/285 |

OTHER PUBLICATIONS

Bognar et al., Acta Chim (Budapest) 58(2), pp. 2203–2205 (1968).
Bognar et al., Magyar Kem Foly 74 (11), pp. 526–530 (1968).
Knoll et al., Orvustudomany 22(3–4), pp. 265–284 (1971).
Bognar et al., Magyar Kem Foly. 78(5), pp. 228–229 (1972).
Knoll et al. II, Archives Internationales de Pharmacodynamie et de Therapie, vol. 210, No. 2, pp. 241–249, 8/74.

*Primary Examiner*—Donald G. Daus
*Assistant Examiner*—Diana G. Rivers
*Attorney, Agent, or Firm*—Karl F. Ross

[57] ABSTRACT

Azidoethylmorphine, a new 7,8-dihydroisomorphine derivative, has excellent antitussive effects without respiration depression.

1 Claim, No Drawings

7,8-DIHYDROISOMORPHINE DERIVATIVE, NAMELY AZIDOETHYLMORPHINE

CROSS REFERENCE TO RELATED APPLICATION

This is a continuation of application Ser. No. 681,214, filed Apr. 28, 1976, which is a continuation-in-part of Ser. No. 502,729 filed Sept. 3, 1974, both now abandoned.

FIELD OF THE INVENTION

This invention relates to a new 7,8-dihydroisomorphine derivative and pharmaceutical products containing the same, as well as to a process for the preparation thereof and a method of treatment.

More particularly, this invention relates to the new compound azidoethyl morphine and pharmaceutically acceptable salts of this compound.

DESCRIPTION OF THE INVENTION

The compound can be prepared according to the invention as follows: the hydroxy groups attached to positions 3 and 6 of the 7,8-dihydromorphine are blocked by appropriate protecting groups, the obtained compound is reacted with a metal azide or a substance furnishing azido groups under the reaction conditions and, if desired, the O-blocking group attached to position 3 of the obtained substance is split off, and/or, if desired, the product is converted into its salt, or the free base is liberated from the salt.

The new compound according to the invention can be used in human therapy primarily as an analgesic agent. It can be administered either alone or together with other morphine derivatives or other biologically active substances.

3-O-ethyl-7,8-dihydromorphine, used as a starting substance in the process according to the invention, is a known compound. The hydroxy groups attached to positions 3 and 6 of the molecules can be protected, prior to azidolysis, by several methods. The hydroxy group in position 3 is protected preferably with an acyl, tetrahydropyranyl or methylenemethoxy group; these groups can be removed either during or after azidolysis.

If 3-substituted derivatives are to be prepared, the hydroxy group attached to position 3 of 7,8-dihydromorphine and of 14-hydroxy-7,8-dihydromorphine is protected with an acyl, alkyl, aralkyl or aryl group, and the protecting group is not removed during or after azidolysis, either.

According to a preferred method of the invention the hydroxy group attached to position 3 is protected by subjecting the dihydroxy compounds to partial acylation, particularly acetylation, formylation or benzoylation. As esterifying agents, preferably the corresponding anhydrides are used, but other esterifying agents can be applied as well.

The hydroxy group attached to position 6 can also be blocked with an acyl group. If more severe acylating conditions are used, the acylation of the hydroxy groups attached to position 3 and 6 takes place simultaneously, and 3,6-diacyl derivatives are formed.

Particularly preferred intermediates for the azidolysis step can be formed by esterifying the hydroxy group in position 6 with an arylsulfonyl or alkylsulfonyl group, among which tosyl, mesyl, brosyl, nosyl and mesityl groups are the most preferred.

If, for example, the hydroxy group in position 3 is blocked by partial esterification using acetic anhydride, and subsequently the hydroxy group in position 6 is esterified with p-toluenesulfonyl chloride, to yield an intermediate compound, the azidolysis is achieved with an excellent yield.

Azidolysis is an important step of the synthesis according to the invention. In this step the substituted hydroxy group in position 6 is replaced by an azido group; this reaction is carried out by contacting the blocked compound with a substance furnishing azido groups. As reagents, metal azides, e.g. sodium or potassium or lithium azide, or substances furnishing azido groups during their decomposition can be used.

The relatively unstable blocking groups attached to position 3 split off easily under the conditions of azidolysis, thus the hydroxy group in position 3 can be unblocked simultaneously with the introduction of the azido group. In this way e.g. a 3-O-acetyl derivative can be converted easily into the corresponding 3-hydroxy compound.

The compounds prepared as described above can be isolated from the reaction mixture either as free bases or in the form of their salts.

The salts obtained in the above reaction can be converted into other salts having greater pharmacological value or more favorable physicochemical properties. Of the salts the tartarates, acetates, salicylates, benzoates, hydrochlorides and formates are to be mentioned.

The new compounds according to the invention can be converted into pharmaceutical compositions suitable for oral, parenteral or rectal administration. The pharmaceutical compositions can be prepared by known techniques, using conventional carriers and/or auxiliary agents.

Azidoethylmorphine possesses outstanding therapeutical properties. When comparing this compound with the most important narcotics and analgesics we have found that it is more effective than any of the known substances with similar biological activities. A further advantage of the new compounds is that addiction occurs less frequently than with other analgesics, which where morphine derivatives are concerned, is an essential factor in judging therapeutic value.

The invention is represented by the following non-limiting Examples.

EXAMPLES

EXAMPLE I 14.85 g. of 3-O-ethyl-7,8-dihydromorphine are dissolved in 60 ml. of absolute pyridine, and a solution of 6.014 g. (4.06 ml.) of methanesulfonyl chloride in 60 ml. of absolute pyridine are added dropwise to the stirred solution within about 20 minutes. During the addition the temperature of the mixture is kept between 0° and 5° C. The mixture is stirred for an additional 2 hours, thereafter allowed to stand at room temperature overnight. The reaction mixture is poured onto 1.5 l. of saturated aqueous sodium hydrocarbonate solution, and extracted with 3×200 ml. of chloroform. The chloroform solutions are combined, washed with 2×100 ml. of water, and dried over magnesium sulfate. The solvents, including pyridine, are removed by distillation, and the obtained resinous substance is dissolved in warm absolute ether. The substance starts soon to crystallize. This way 11.86 g. (64%) of 6-O-mesyl-dihydrodionine are obtained; m.p.: 135°–136° C., $(\alpha)_D = -96.1°$ (c=0.52, in chloroform).

EXAMPLE II 11.0 g. of 6-O-mesyl-dihydro-dionine are dissolved in 330 ml. of dimethylformamide, and a solution of 18.19 g. of sodium azide in 51.2 ml. of water is added. The homogeneous reaction mixture is warmed at 100° C. for 24 hours, thereafter cooled and poured onto 1.65 l. of water. The aqueous solution is extracted with 4×200 ml. of chloroform. The chloroform solutions are combined, washed with 2×110 ml. of saturated aqueous sodium chloride solution, dried over magnesium sulfate, filtered, and the filtrate is evaporated at a temperature not exceeding 50° C. The obtained resinous product is dissolved in absolute ether. The separated fluffy substance is filtered off, and the filtrate is evaporated to dryness. 6.8 g. of a pure, resinous substance are obtained. This substance is dissolved in 102 ml. of dry ethanol, and a hot solution of 3 g. of D-tartaric acid in 30 ml. of ethanol is added. The tartrate separates as yellow crystal plates. The product is recrystallized twice from water. This way 3-O-ethyl-6-deoxy-6-azido-7,8-dihydroisomorphine (azidoethyl morphine) bitartrate, melting at 55°–56° C., is obtained. $(\alpha)_D = -192°$ (c=0.5, in chloroform).

The bitartrate is dissolved in water, and the solution is rendered alkaline with sodium carbonate, to yield crystalline 3-O-ethyl-6-deoxy-6-azido-7,8-dihydroisomorphine (azidoethyl morphine).

Antitussive activity. The antitussive activity in rats was tested by the method of Gosswald (1). Wistar rats weighing 130–180 g were placed in a plexi box (23×22×11 cm) and cough responses were elicited by citric acid aerosol (10%). The latency period of cough was measured before and after drug administration. The control latency was determined 18 hours before the drug administration. Animals with less than 60 sec control latency were used for the experiments. The average control latency was found to be 29.41±9.61 sec. Each animal was exposed to citric acid aerosol for a 3 min period 30 and 60 min after drug administration. The dose of a drug which inhibited coughing over 90 sec was considered effective. Ten animals were used at each dose level. The antitussive dose (AtD$_{50}$) was calculated according to Litchfield and Wilcoxon (2). The drugs were administered by subcutaneous and oral routes.

Antitussive activity in cats was determined by the method of Domenjoz (3). Cats weighing 2.5–3.5 kg were anaesthetized with an i.p. dose of 30 mg per kg of sodium pentobarbitone. The superior laryngral nerve was exposed and cough was induced by electrical stimulation of the nerve (1 msec, 10 Hz, 5–10 V for 10 sec) through bipolar platinum electrodes every five minutes. The cough responses were measured by means of a Marey-tambour connected to a face mask, and recorded on a smoked paper. Drugs were given intravenously in increasing doees. The effect of each dose was measured on at least five cats. Effects of the drugs were calculated from the changes in amplitude of cough curves. If no coughing was produced by two successive stimulations, the dose was taken as the effective antitussive dose (AtD$_{100}$). The antitussive dose (AtD$_{50}$) which reduces the control response by 50 percent was calculated by the method of Litchfield and Wilcoxon (3).

Respiratory effects. Effects on respiration were determined by means of Krogh-equipment. Respiratory frequency, depth and minute volume were calculated from the Krogh curves. Changes in respiration were determined before drug administration and after injecting doses at the AtD$_{100}$ level. Five animals were used for each substance.

Circulatory effects. Blood pressure changes were studied in cats anaesthetized with pentobarbitone sodium (35 mg/kg$^{-1}$, i.p). The substances were injected into the right femoral vein, responses to drugs were measured by means of a mercury manometer and recorded on a smoked cylinder. Since the hypotensive effects or morphine decrease on repeated administration (4), the blood pressure changes were calculated from the responses to the very first injections of the substances.

Compounds. Codeine HCl, azidocodeine bitartrate, 14-OH-azidocodeine bitartrate, hydrocodone base, oxycodone base, morphine HCl, azidomorphine bitartrate, 14-OH-azidomorphine bitartrate, hydromorphone base, oxymorphone base, ethylmorphine HCl, azidoethylmorphine bitartrate, pholcodine base, azidopholcodine base (Alkaloida Pharmaceutical Works, Hungary).

Antitussive effects. Tables I and II show the results of antitussive testing in cats and rats. The antitussive effect of azidomorphine in the cat was formed to be dose-dependent. An i.v. dose of 0.25–0.50 mg.kg$^{-1}$ of nalorphine antagonized the antitussive effects of all investigated drugs.

The data in Tables I and II demonstrate that azidomorphines are the most potent antitussives among the semisynthetic morphine derivatives hitherto known.

Effects on respiration. Table III shows the effect of the alkaloids on respiration in the cat expressed by the ratios of different breathing parameters (respiratory frequency, depth and minute volume) measured before and after administration of the AtD$_{100}$ of the test compound. The azidomorphines (except 14-hydroxy-azidocodeine) did not influence respiration, but 5 out of the 8 non-azids depressed significantly at least one of the respiratory parameters.

TABLE I

| | Inhibitory activity of azidomorphine derivatives and reference antitussives on citric acid aerosol induced cough in rats | | | |
|---|---|---|---|---|
| Compounds | AtD$_{50}$ mg. kg.$^{-1}$ s.c. | Ratio codeine/ drug | AtD$_{50}$ mg. kg.$^{-1}$ oral | Ratio codeine/ drug |
| Codeine | 19.0(15.08–23.94) | 1.00 | 100.0(66.67–150.00) | 1.00 |
| Hydrocodone | 0.90(0.61–1.37) | 21.11 | 16.0(8.89–28.80) | 6.25 |
| Oxycodone | 1.40(1.15–1.71) | 13.57 | 3.5(2.08–5.88) | 28.57 |
| Azidocodeine | 1.57(1.29–2.41) | 12.10 | 2.5(1.69–3.70) | 40.00 |
| 14-OH-azidocodeine | 0.82(0.71–0.95) | 23.17 | 3.2(2.00–5.12) | 31.25 |
| Morphine | 3.00(1.84–4.25) | 6.33 | 74.0(51.03–107.30) | 1.35 |
| Hydromorphone | 0.26(0.22–0.30) | 73.07 | 17.5(13.46–22.75) | 5.71 |
| Oxymorphone | 0.058(0.052–0.065) | 327.58 | 14.0(11.45–15.38) | 7.14 |
| Azidomorphine | 0.034(0.023–0.049) | 558.82 | 9.0(4.74–17.01) | 11.11 |

TABLE I-continued
Inhibitory activity of azidomorphine derivatives and reference antitussives on citric acid aerosol induced cough in rats

| Compounds | AtD$_{50}$ mg. kg.$^{-1}$ s.c. | Ratio codeine/ drug | AtD$_{50}$ mg. kg.$^{-1}$ oral | Ratio codeine/ drug |
|---|---|---|---|---|
| 14-OH-azidomorphine | 0.021(0.013–0.035) | 904.76 | 10.0(7.40–13.50) | 10.00 |
| Ethylmorphine | 34.4(27.31–43.34) | 0.55 | 103.2(92.14–152.22) | 0.97 |
| Azidoethylmorphine | 3.5(2.37–5.18) | 5.42 | 1.67(1.14–2.44) | 59.88 |
| Pholcodine | 30.00(20.00–45.00) | 0.63 | — | — |
| Azidopholcodine | 4.5(3.04–6.66) | 4.22 | 460.0(396.60–533.60) | 0.22 |
| Oxymethebanol | 7.0(4.93–9.94) | 2.71 | 24.0(17.8–32.4) | 4.16 |

Values in brackets indicate 95% confidence limits.

Table II
Inhibitory activity of azidomorphine derivatives and reference antitussives on electrical stimulation induced cough in cats

| Compounds | AtD$_{50}$ mg. kg$^{-1}$ i.v. | Ratio Codeine/ drug | AtD$_{50}$ mg. kg$^{-1}$ i.v. | Ratio Codeine/ drug |
|---|---|---|---|---|
| Codeine | 1.45 | 1.00 | 5.07 ± 1.87 | 1.00 |
| Hydrocodone | 0.20 | 7.25 | 0.56 ± 0.07 | 9.05 |
| Oxycodone | 0.20 | 7.25 | 0.44 ± 0.07 | 11.52 |
| Azidocodeine | 0.40 | 3.63 | 1.08 ± 0.04 | 4.69 |
| 14-OH-azidocodeine | 0.60 | 2.42 | 1.47 ± 0.07 | 2.91 |
| Morphine | 0.61 | 2.38 | 1.28 ± 0.32 | 3.96 |
| Hydromorphone | 0.026 | 55.76 | 0.064 ± 0.001 | 79.21 |
| Oxymorphone | 0.016 | 80.55 | 0.032 ± 0.005 | 158.43 |
| Azidomorphine | 0.006 | 241.66 | 0.018 ± 0.002 | 281.66 |
| 14-OH-azidomorphine | 0.012 | 120.83 | 0.020 ± 0.002 | 253.50 |
| Ethylmorphine | 2.58 | 0.56 | 8.32 ± 1.56 | 0.61 |
| Azidoethylmorphine | 0.54 | 2.69 | 0.84 ± 0.29 | 6.03 |
| Pholcodine | 8.8 | 0.16 | 12.7 ± 1.41 | 0.40 |
| Azidopholcodine | 2.0 | 0.73 | 3.5 ± 0.48 | 1.45 |

Table III
Respiratory changes due to various drugs given in doses producing total cough depression in cats

| Compounds | Frequency after AtD$_{100}$ per control frequency | Depth after AtD$_{100}$ per control depth | Min. volume after AtD$_{100}$ per control minute volume |
|---|---|---|---|
| Codeine | 0.82 ± 0.03[1] | 0.83 ± 0.03[1] | 0.70 ± 0.04[1] |
| Hydrocodone | 0.90 ± 0.05[1] | 0.93 ± 0.03 | 0.84 ± 0.05[1] |
| Oxycodone | 0.84 ± 0.05[1] | 0.91 ± 0.04 | 0.78 ± 0.07[1] |
| Azidocodeine | 0.82 ± 0.09 | 0.97 ± 0.13 | 0.81 ± 0.14 |
| 14-OH-azidocodeine | 0.88 ± 0.05[1] | 0.93 ± 0.08 | 0.67 ± 0.07[1] |
| Morphine | 0.78 ± 0.07[1] | 0.79 ± 0.06[1] | 0.62 ± 0.07[1] |
| Hydromorphone | 1.09 ± 0.12 | 0.80 ± 0.07[1] | 0.85 ± 0.08 |
| Oxymorphone | 0.92 ± 0.10 | 0.99 ± 0.23 | 0.91 ± 0.12 |
| Azidomorphine | 0.94 ± 0.06 | 0.97 ± 0.05 | 0.93 ± 0.06 |
| 14-OH-azidomorphine | 0.91 ± 0.10 | 1.02 ± 0.15 | 0.88 ± 0.08 |
| Ethylmorphine | 0.85 ± 0.02 | 0.72 ± 0.24 | 0.65 ± 0.14 |
| Azidoethylmorphine | 0.95 ± 0.10 | 0.91 ± 0.05 | 0.88 ± 0.13 |
| Pholcodine | 1.17 ± 0.07 | 0.90 ± 0.06 | 1.05 ± 0.04 |
| Azidopholcodine | 1.15 ± 0.13 | 0.88 ± 0.06 | 1.02 ± 0.16 |

Means ± S.E.—n = 5.—[1]$P < 0.05$ (Student test).

We claim:
1. 3-O-ethyl-6-deoxy-6-azido-7,8-dihydroisomorphine or a pharmaceutically acceptable salt thereof.